March 13, 1973 O. RIEGER Plant Pat. 3,319
BEGONIA PLANT
Filed June 30, 1971
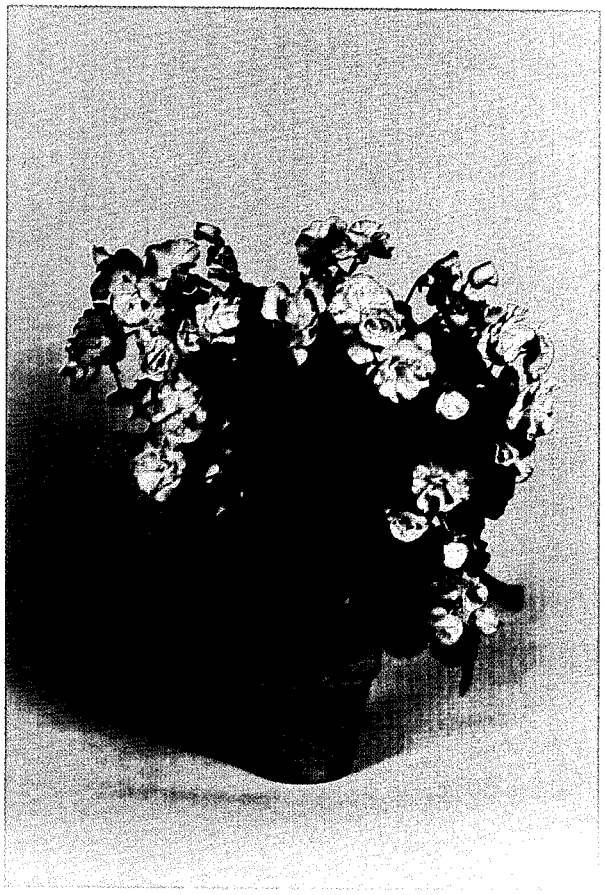

United States Patent Office

Plant Pat. 3,319
Patented Mar. 13, 1973

3,319
BEGONIA PLANT

Otto Rieger, deceased, by Gertrud Rieger, legal representative, Nurtingen, Germany, assignor to Mikkelsens, Inc., Ashtabula, Ohio Filed June 30, 1971, Ser. No. 158,641
Int. Cl. A01h 5/00
U.S. Cl. Plt.—68 1 Claim The present invention herein described relates to a new and distinctive variety of begonia plant botanically known as *Begonia elatior,* discovered by me as a color mutation of an *elatior* hybrid begonia commercially known as Rieger's Aphrodite. This mutation was found in nurseries in Nurtingen, Germany, and through asexual reproduction by stem, leaf and terminal cuttings, the new variety has been found to retain its distinctive characteristics through successive propagations.

The main distinguishing feature of the new variety is the coloring of the cherry red petals of the double azalea-like flowers compared to the light rose red coloring of the flowers of the parent variety. A characteristic which further distinguishes the new variety from the parent is its ability to propagate both by leaf and terminal tip cuttings. The use of leaf cuttings for asexual propagation is of substantial economic importance. The overall growth is somewhat more rapid than the growth of the parent variety.

The following characteristics distinguish the new variety from other commercial begonia varieties of this general type:

(1) The flowers are quite numerous and borne on trusses that because of the combined weight of the flowers need support unless they are used for cascading or trailing displays.

(2) The flowers are double azalea type, possessing very few if any reproductive parts.

(3) The flowers are very durable and long lasting, with continuous flowering in the summer period for three to four months.

(4) Overall plant growth is compact. Self-branching is prominent, giving full body to the terminal areas of the plant. Rhizomatous growth fills in the base of the plant.

(5) Overall growth is somewhat soft under poor light conditions, necessitating some staking support.

(6) Foliage is dark green with a distinctive thin edging of red pigmentation. Young foliage has an infusion of red that eventually is masked on the upper surface as the leaf matures. The foliage is quite resistant to the common foliar disorders of begonias, especially mildew and botrytis.

(7) The soft type growth that occurs during the early spring months or in long periods of restricted sunlight allows the new variety to be grown as a cascading or hanging basket type developing trailing trusses of flowers several feet in length in a short period of time. This is of significant economic importance in begonia culture.

The accompanying colored photograph illustrates the flowering of a supported plant and shows typical foliage and overall growth of the new variety, with the photograph being as true as it is reasonably possible to reproduce in color photographs of this type.

The following detailed description of the new variety is based on observations made of the new variety when grown by established commercial methods in Nurtingen, Germany. Color references are to the Royal Horticultural Society Colour Chart, except where general color terms of ordinary dictionary significance are used.

Parentage: Mutation from a previous Rieger elatior begonia hybrid commercially known in Europe as Rieger's Aphrodite. The mutation was found in greenhouses in Nurtingen, Germany.

Propagation: Consecutive asexual propagation indicates that this variety is capable of being reproduced true to type. Terminal cuttings and stem cuttings root in approximately three weeks time using 20° C. temperature in the propagation media. Leaf cuttings will root in three to four weeks with propagation media at 20° C. Rhizomes will emerge in an additional eight to ten weeks with propagation media at 18° C.

Rooting habit: Roots are abundant, fine textured and respond rapidly in loose, well aerated composts.

Plant form: Plants are semidwarf, generally compact and full as a result of freely self-branching characteristics. Leaf internodes are close. Overall growth is somewhat more rapid than the original parent variety.

Habit of growth: Vigorous and upright under good natural light conditions. Plants need support during poor light periods of the year. The new variety can be cultivated for a trailing or cascading type during the periods of low light intensity because of its soft flexible character under such conditions.

Blooming habits: Flowering is initiated during short days and 18° C. temperature. Both the new variety and the parent flower continuously during the summer similarly to *Begonia semperflorens.*

Blooming season: Under appropriate greenhouse cultural techniques, this variety can be brought into flower any season of the year. It is best adapted for late spring, summer, and early fall seasons.

Foliage: Alternate: borne at close angle to the stem being average to above average in quantity. Foliage feels somewhat waxy or greasy and is quite resilient to normal handling.

(*a*) *Size.*—Medium for commercial begonias at maturity, being approximately 6 to 10 cm. long by 4 to 8 cm. wide. Environmental and general plant conditions can greatly alter the size and color of the foliage.

(*b*) *Shape.*—Oval pointed, heart shaped with either one lobe or the other on either side of the petiole being longer.

(*c*) *Texture.*—Upper side—smooth, leathery, waxy or greasy to the feel but somewhat flat in appearance. Under side—smooth, glossy, highly reflective.

(*d*) *Margin.*—Indented and sharply serrated on new foliage, losing some definition at maturity. The foliage has a definite and distinctive narrow red edge.

(*e*) *Color.*—New foliage-upper side near RHS 143 A with some red infusion; under side near RHS 146 C. Old foliage—upper side near RHS 135 A; under side near RHS 146 B with some red infusion.

Disease resistance: The foliage is quite resistant to both mildew and botrytis as tested with susceptible begonia varieties under normal cultural conditions of the greenhouse.

Flowers: Double azalea type that show very few if any reproductive parts.

(*a*) *Borne.*—On trusses with multiple clusters. If trusses are trained for trailing or cascading hanging basket types, the flower truss can develop under optimum conditions to several feet in length in a relatively short period of time. The extreme long lasting quality of the individual blooms is a beneficial character for this type of specimen. Bloom size is relative to the number of blooms produced per plant but often measures 4 to 6 cm. across.

(*b*) *Quantity.*—Extremely floriferous, unusually long lasting, and continuously flowering over a relatively long period of time.

(*c*) *Petal color.*—RHS 50 A, fading to 50 B.

(*d*) *Buds.*—Develop progressively at the nodes to the size and shape of a lima bean, approximately 2 cm. in diameter before opening. The lighter reverse coloring can be seen before opening.

(*e*) There are insufficient reproductive parts to be described.

What is claimed:

1. A new and distinctive variety of begonia characterized by its numerous double azalea type flowers which have superior durability and long lasting qualities and which continuously flower in the summer period for three to four months, its compact growth habit and prominent self-branching, its dark green, resistant, foliage which has a distinctive thin edging of red pigmentation, and characterized particularly when compared with the parent variety Rieger's Aphrodite by its cherry red flower color, its rapid overall growth, and it ability to be asexually reproduced by stem, leaf or terminal cuttings.

No references cited.

R. E. BAGWILL, Primary Examiner